United States Patent [19]

Linnenbach

[11] Patent Number: 5,185,254
[45] Date of Patent: Feb. 9, 1993

[54] GENE FAMILY OF TUMOR-ASSOCIATED ANTIGENS

[75] Inventor: Alban Linnenbach, Philadelphia, Pa.

[73] Assignee: The Wistar Institute, Philadelphia, Pa.

[21] Appl. No.: 291,583

[22] Filed: Dec. 29, 1988

[51] Int. Cl.⁵ .................. C12N 15/00; C12P 21/06; C07K 13/00; C07H 21/00

[52] U.S. Cl. .................. 435/172.3; 435/69.1; 435/69.3; 435/71.1; 935/1; 935/6; 935/12; 935/60; 530/395; 530/828; 536/23.5

[58] Field of Search .................. 435/69.3; 935/1, 12, 935/60; 530/395, 828

[56] References Cited

PUBLICATIONS

Beauchemin et al Mol Cell Biol 7(9):3221, 1987.
Ross et al Biochem Biophys Res. Comm. 135:297, 1986.
Proc. Natl. Acad. Sci. USA, vol. 87, pp. 3542-3546, dated May 1990 Entitled: "Molecular cloning of cDNA for the carcinoma-associated antigen GA733-2", by Stanislaw Szala, et al.

*Primary Examiner*—John Doll
*Assistant Examiner*—Suzanne Ziska
*Attorney, Agent, or Firm*—Banner, Birch, McKie & Beckett

[57] ABSTRACT

A tumor-associated antigen, GA733-1, has been discovered which shares sequence homology with both thyroglobulin type I and interleukin-2 receptors. The antigen is highly expressed in pancreatic carcinoma cells. The antigen is similar to a previously described tumor-associated antigen found in colorectal carcinoma cells. The gene for the antigen is fully sequenced and described here.

4 Claims, 4 Drawing Sheets

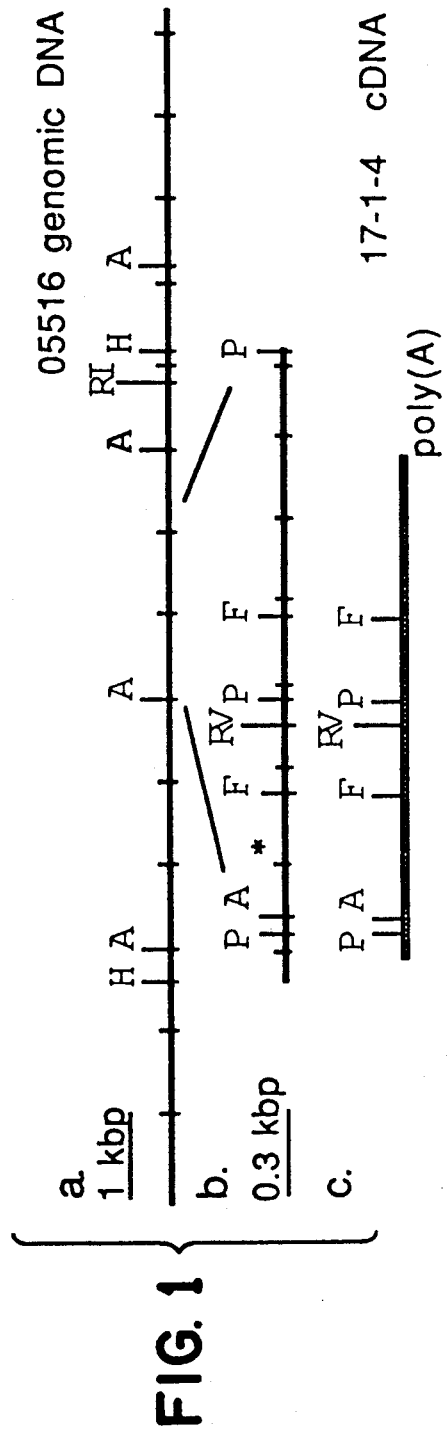

FIG. 2A

GENE FAMILY OF TUMOR-ASSOCIATED ANTIGENS

BACKGROUND OF THE INVENTION

The U.S. government has a paid-up license in this invention and the right in limited circumstances to require the patent owner to license others on reasonable terms as provided for by the terms of Grant No. CA 21124-11 from the National Institutes of Health.

FIELD OF THE INVENTION

This invention relates to tumor-associated antigens which are members of a gene family. More particularly, this invention relates to a tumor-associated antigen which is strongly expressed in pancreatic carcinoma cells.

BACKGROUND OF THE INVENTION

Monoclonal antibodies denominated MoAb GA733, raised against a human stomach adenocarcinoma cell line, have been extensively evaluated for the diagnosis and therapy of human gastrointestinal tumors. See, e.g. Herlyn, et al. Hybridoma, vol. 5, Suppl. 1, 1986, pp. S3-S10. GA733 antibodies bind to a variety of tumors of the gastrointestinal tract, including prostate, cervix, ovarian, bladder, lung, breast, colorectal, and pancreatic carcinomas. In addition, the GA733 antibodies bind in varying degrees to normal epithelial tissues.

GA733 antibodies have been shown to inhibit the growth of tumor xenografts in nude mice. (Herlyn et al., (1980) Cancer Res. vol. 40, pp. 712-721; and Herlyn et al., (1984) J. Immunol. Methods, vol. 73, pp. 157-167.) In addition, these antibodies have been used to obtain anti-idiotypic antibodies which bear the internal image of the GA733 tumor antigen. The anti-idiotypic antibodies, when used as an immunogen, were able to elicit in two species of animals anti-antiidiotype antibodies, which have a binding specificity similar to that of the original GA733 antibodies. (Herlyn, et al. (1986) Science, vol. 232, pp. 100-102.)

GA733 antibodies immunoprecipitate a 40 kd cell surface glycoprotein isolated from colorectal tumor cells. However, it is difficult to obtain sufficient quantities of tumor antigen for immunizations. Thus, there is a need in the art for a means of producing substantial quantities of tumor-associated antigens such as GA733 antigen. Further, there is a need for other antibodies which react with different epitopes on the GA733 antigen. Additionally, there is a continuing need for different tumor-associated antigens than those already known.

SUMMARY OF THE INVENTION

It is an object of the invention to provide a segment of DNA which codes for the GA733-1 antigen.

It is another object of the invention to provide a cell line which produces GA733-1 antigen.

It is still another object of the invention to provide a method of producing an immunogen which comprises one or more epitopes of the GA733-1 antigen.

It is yet another object of the invention to provide a method of treating a human carcinoma.

It is stil another object of the invention to provide a preparation of antibodies which are immunoreactive with GA733-1 antigen but not with GA733-2 antigen.

It is another object of the invention to provide a substantially pure polypeptide encoded by the DNA sequence for GA733-1 antigen.

It is yet another object of the invention to provide an oligonucleotide probe for detecting members of the gene family comprising the GA733-1 and GA733-2 antigens. These and other objects of the invention are provided in one or more of the embodiments which are described below.

In one embodiment, a segment of DNA is provided which codes for the GA733-1 antigen. A physical map of the DNA is illustrated in FIG. 1; the sequence coding for the antigen is shown in FIG. 2.

In another embodiment of the invention, a cell line which has been genetically engineered to replicate and express the DNA sequence of the GA733-1 antigen is provided.

In another embodiment of the invention, a method of producing an immunogen is provided which comprises culturing cells which have been genetically engineered to replicate and express the DNA sequence which codes for the GA733-1 antigen; and then harvesting a protein fraction from said cells or culture medium.

In yet another embodiment of the invention, a method of treating a human carcinoma is provided which comprises administering an effective amount of a preparation comprising one or more epitopes of the GA733-1 antigen to a patient bearing a carcinoma, to stimulate production of antibodies immunoreactive with said antigen.

In another related embodiment, a method is provided for treating a human carcinoma in which antiidiotypic antibodies which have the ability to stimulate production of antibodies which immunoreact with antigen GA733-1 are administered to the patient, and then an effective amount of a preparation comprising one or more epitopes of the antigen GA733-1 is administered to said patient to further stimulate production of antibodies which immunoreact with antigen GA733-1.

In still another embodiment of the invention, a preparation of antibodies are provided which are immunoreactive with GA733-1 antigen but not with the GA733-2 antigen.

In another embodiment of the invention, a substantially pure polypeptide is provided which is encoded by the DNA sequence shown in FIG. 2.

In yet another embodiment of the invention, a cell line is provided which has been genetically engineered to replicate and express the DNA sequence of the GA733-1 antigen.

In another embodiment of the invention, an oligonucleotide probe is provided for detecting members of the gene family comprising GA733-1 and GA733-2. The probe encodes the amino acid sequence of the first 18 amino acids of antigen GA733-2.

The present invention provides the art with an hitherto unknown tumor-associated antigen. While related to the well-studied tumor antigen GA733-2, it is substantially different in its sequence, thus providing new epitopes to the art as targets for anti-tumor immunotherapy.

BRIEF DESCRIPTION OF THE DRAWINGS

FIG. 1 depicts the relationship between the GA733-1 chromosomal gene and its full-length cDNA. Line a shows the restriction map of the genomic clone; line b shows the 2.2 kb genomic region that was sequenced;

line c shows the restriction map of a placental cDNA clone.

FIG. 2 shows the complete DNA sequence of the chromosomal gene GA733-1.

FIG. 3 shows a sequence comparision between the two members of the GA733 gene family. The sequence shown for GA733-1 is the predicted amino acid sequence on the basis of the nucleotide sequence, and that shown for GA733-2 is the empirically determined amino acid sequence of the GA733-2 antigen.

Figure 4:
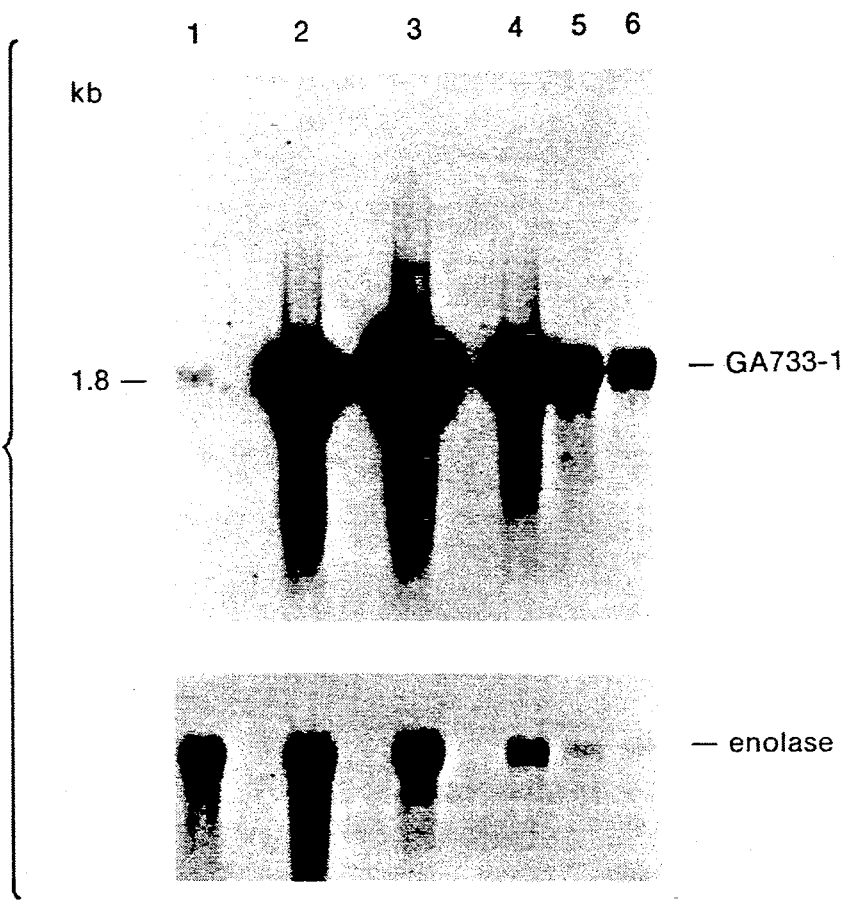

FIG. 4 shows a northern blot analysis of GA733-1 mRNA in gastrointestinal tumor cell lines, including colorectal carcinoma cell line (shown in lane 1) and pancreatic carcinoma cell lines (shown in lanes 2 and 3).

DETAILED DESCRIPTION OF THE INVENTION

It is a discovery of the present invention that the well-known and studied tumor-associated antigen which is reactive with monoclonal antibody GA733 is a member of a family of antigens which are tumor associated. A new antigen (termed herein GA733-1) has been found, which is different yet similar to the antigen which is found in human colorectal adenocarcinoma cells and which is immunoreactive with GA733 monoclonal antibodies. The amino acid sequence of GA733-1 antigen is identical to that of native GA733-2 antigen at 19 out of the first 30 amino acid residues of the latter protein, with conservative substitutions occurring at three other positions. In addition, a rare amino acid motif of cysteine-tryptophan-cysteine occurs at positions 36 to 38 of GA733-2 protein and is also present at the corresponding position in the GA733-1 sequence.

The two antigen sequences have been compared using ALIGN, a computer program in which similarities between two protein sequences are expressed as standard deviation units (s.d.) above the mean score of 100 random runs. According to this program, a score between three and eight s.d. is indicative of a possible relationship between the two sequences; scores greater than eight s.d. are considered highly significant. The two GA733 sequences, when compared over the first 30 amino acid residues, yielded a similarity score of 17 s.d. units. The similarity of the two protein sequences indicates that there is a gene family of at least two closely related genes. The sequence comparison between the two proteins is shown in FIG. 3.

The amino-terminal 45 residues of the 30 kd form of the GA733-2 antigen correspond to sequences located 90 residues from the proposed amino terminus of the GA733-1 antigen. It is suggested that the amino-terminal 90 residues (about 10 kd) of the GA733-2 antigen were cleaved off giving rise to the 30 kd breakdown product. This is consistent with the fact that two forms of the GA733-2 antigen were purified from SW948 human colorectal adenocarcinoma cell line, one being 40 kd and one being 30 kd.

A segment of DNA according to the present invention is a DNA sequence which has been isolated from the human chromosome in which it is naturally located. The DNA segment contains the sequence for the GA733-1 antigen. The sequence of this DNA segment has been determined and is shown in FIG. 2. The sequence shown is thought to represent the entire gene because it corresponds in sequence to the full-length cDNA, without interruption by introns.

Figure 2A:
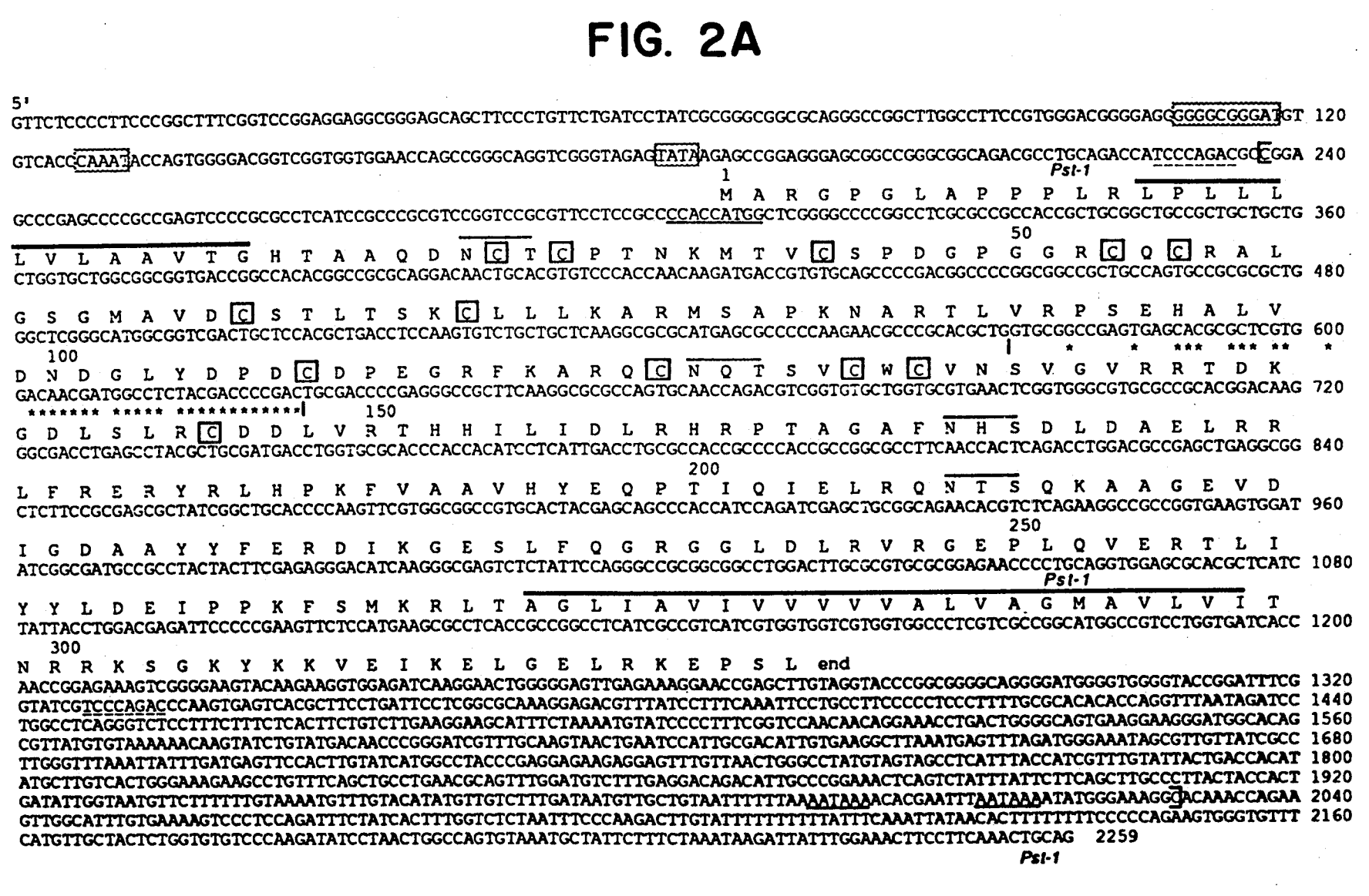
Figure 2B:
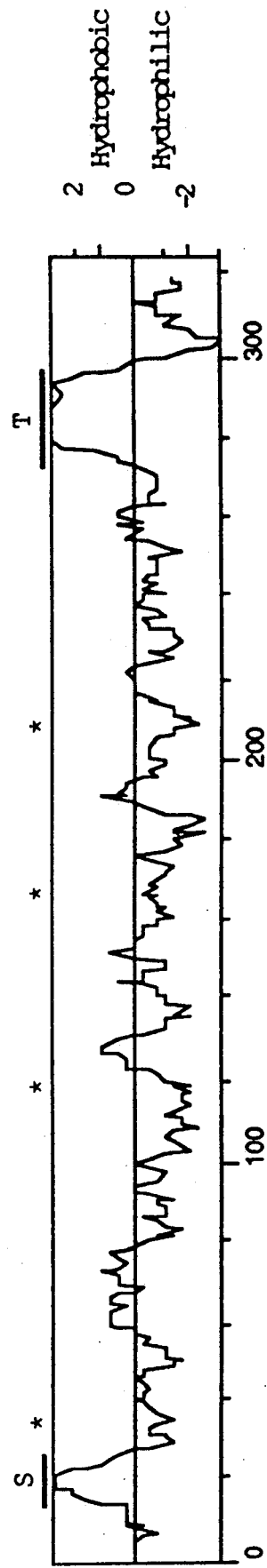

The protein which is predicted from the DNA sequence shown in FIG. 2 is characterized by a putative signal sequence with a 13 residue hydrophobic core; this is marked by an overline in the figure and spans nucleotide number 360. An extracellular domain, rich in cysteine residues (which are boxed in the figure) and containing four potential N-linked glycosylation sites (indicated by an overline) is found between amino acid residues approximately 25 and 270. A single 23-residue transmembrane domain is indicated at amino acid residues approximately 275 to 300. The cytoplasmic domain consists of a positively charged, 26 residue segment. The positions which correspond to the 5' and 3' ends of the full-length cDNA clone are marked with brackets. FIG. 2B shows a Kyte-Doolittle plot of the sequence of the protein. Structural features illustrated include the putative hydrophobic signal peptide (S), the hydrophilic extra-cellular domain containing potential N-linked glycosylation sites (*), the hydrophobic transmembrane domain (T), and the short, hydrophilic cytoplasmic domain.

As used herein the antigen which has been defined on the basis of its complete DNA sequence, is termed GA733-1. The related antigen which has been isolated from human colorectal adenocarcinoma cells and binds to monoclonal antibodies CO17-1A and GA733 is termed herein GA733-2 antigen. These two antigens form a family of tumor-associated antigens. Interestingly, both the GA733-1 and the GA733-2 sequences have been found to be homologous to the human and bovine thyroglobulin type I repeat unit. The thyroglobulin type I repeat units consist of 10 copies of a 60-amino acid sequence located at the amino-terminal end of the molecule. Comparing the sequence of GA733-1 with the human and bovine type I repeates using the program ALIGN, a similarity score of 14 s.d. units was obtained, establishing the high statistical significance of the homology between these proteins. The two GA733 sequences also share some homology with the alpha subunit of the interleukin-2 receptor. However, using the program ALIGN, the highest alignment score obtainable was only 7.5 s.d. units. Thus, the homology of the tumor-associated antigens to interleukin-2 receptor is less significant than the homology to the thyroglobuline proteins.

An immunogen according to the present invention is any preparation, usually protein or glycoprotein, which, when administered to an animal, stimulates the production of antibodies immunoreactive with that antigen. Methods of administering immunogens to animals are well known in the art, and can be accomplished by any of the known means, including: subcutaneous, intramuscular, and intraperitoneal injections. Determination of amounts which are to be used to stimulate antibody production is within the skill of the art. Formulations which are pharmaceutically suitable are also well known in the art. Generally, these may comprise general immunological adjuvants to stimulate the immune system.

In some cases the preparation which is administered to stimulate antibody production does not contain the entire protein coded by the GA733-1 gene. It may be desirable that a polypeptide comprising one or more epitopes of the antigen be administered. This will provide for greater specificity of the immune response, and may provide lower cost alternatives than use of the full-length protein.

Anti-idiotypic antibodies may also be used to stimulate production of the antibodies which immunoreact with antigen GA733-1. Such antibodies are known in the art. See, Herlyn, et al., (1986) Science, vol. 232, pp. 100–102. In addition, other anti-idiotypic antibodies can be produced using the polypeptides of the present invention. For example, polypeptides bearing one or more epitopes of antigen GA733-1 may be used to stimulate production of a variety of antibodies immunoreactive with antigen GA733-1. Particular immunoreactive antibodies can then be used to raise anti-idiotypic antibodies by administering these anti-GA733-1 antibodies into other animals. Methods of selection of true anti-idiotypic antibodies are known in the art; however, availability of the GA733-1 antigen or polypeptides containing one or more epitopes of the antigen will make screening for proper anti-idiotypic antibodies more rapid and selective. Briefly, proper anti-idiotypic antibodies can be screened for the ability to bind to antibodies directed against the GA733-1 antigen; the binding of anti-idiotypic antibodies can be competed off with use of the antigen or polypeptides containing one or more epitopes of the antigen. In addition, anti-idiotypic antibodies can be screened for the ability to themselves stimulate production of antibodies (anti-anti-idiotypic antibodies, AB3) which are able to themselves bind directly to the tumor antigen GA733-1.

A preparation of antibodies are provided by the present invention which are immunoreactive with GA733-1 antigen but not with GA733-2 antigen. Such antibodies may be polyclonal or monoclonal. Polyclonal antibodies, which are well known in the art, can be made monospecific by immunoabsorption techniques which are also known in the art. Briefly, GA733-2 antigen can be bound to an inert matrix to form an immuno-affinity column. Antibodies raised against the GA733-1 antigen can be passed over such a column or matrix to remove from the preparation all those antibodies which are cross-reactive with the GA733-2 antigen. Those antibodies which do not bind to the GA733-2 immunoaffinity column can be collected and form a preparation of antibodies which are immunoreactive with GA733-1 antigen but not with GA733-2 antigen. Similarly, monoclonal antibodies which have been raised against the GA733-1 antigen can be screened for the ability to bind to GA733-1 antigen, and the lack of binding ability toward GA733-2 antigen. Once again, such antibody production methods and screening methods are well known in the art.

Substantially pure polypeptides are provided by the present invention which contain one or more epitopes of the antigen GA733-1. Such polypeptides can be easily synthesized according to the sequence of the GA733-1 antigen shown in FIG. 2. Once polypeptides have been synthesized, they can be tested for their immunogenicity by standard immunological tests, either involving binding to known antibodies or by raising antibodies by administration of the polypeptide to an animal to induce antibodies. Antibodies which result may be tested for immunoreactivity with the GA733-1 antigen itself. Polypeptides which are able to stimulate production of GA733-1-reactive antibodies bear one or more epitopes of GA733-1. Methods for synthesizing polypeptides are well known in the art. Substantial purity, according to the present invention, means that the polypeptide will be free of other human proteins.

An oligonucleotide probe is also provided by the present invention for detecting additional members of the gene family which comprises the antigens GA733-1 and GA733-2. Such probes may be made according to the DNA sequence of GA733-1, shown in FIG. 2, or according to the amino acid sequence determined for the isolated and purified GA733-2 antigen. One such probe encodes the amino acid sequence of the first about 18 amino acids of antigen GA733-2. This probe as well as other can be used to detect members of the gene family by hybridization to chromosomal DNA, cDNA, or mRNA under low stringency conditions to locate homologous and related genes. Such hybridization techniques are well known in the art. An alternative means for detecting members of the gene family comprising GA733-1 and GA733-2 is to use monoclonal antibodies which are reactive with antigens of the gene family, such as CO17-1A and GA733, to detect clones from human cDNA libraries which express proteins which are cross-reactive with such antibodies.

A cell line is also provided by the present invention which replicates and expresses the DNA sequence of the GA733-1 antigen. Such expression is accomplished by genetic engineering of a cell line which does not express the GA733-1 antigen. Such engineering involves putting the GA733-1 gene into the cell line in a manner such that it is replicated and expressed. Typically this can be accomplished by incorporating the GA733-1 gene into a plasmid which contains a viral promoter or other suitable eukaryotic promoter upstream from the GA733-1 gene. Other methods for introducing and expressing genes in cell lines are known in the art and can be used.

The following examples are not intended to define the scope of the invention. The scope of the invention is defined by the claims appended below.

EXAMPLE 1

This example demonstrates the purification of the GA733-2 antigen from colorectal carcinoma cells.

The GA733-2 antigen was isolated by immunoaffinity chromatography from detergent extracts of SW948 tumors propagated in nude mice, as described (Ross, A. H., et al., (1986) Biochem. Biophys. Res. Commun. 135, 297–303) except that the detergent was omitted from the basic buffer used to elute the antigen from the GA733 antibody column. The fractions judged by Western blotting to contain GA733-2 antigen were pooled, dialyzed against 0.05M $NH_4HCO_3$, and lyophilized. The protein was reduced and alkylated with iodoacetic acid and separated from salts and low-molecular weight impurities by chromatography using a column of LH-20-Sephadex (1.4×5.5 cm), equilibrated with 88% formic acid/ethanol/water (20:50:30) (Marano, N., et al., (1987) J. Neurochem. 48, 225–232). This material was judged to be pure by $NaDodSO_4$-PAGE and silver staining. 40 kd and 30 kd species were observed, the latter thought to represent a proteolytic breakdown product of the 40 kd antigen.

EXAMPLE 2

This example demonstrates the amino acid sequence determination of GA733-2 antigen isolated from colorectal carcinoma cells.

Several amino-terminal sequence runs were performed using amounts ranging from 100–500 pmoles of carboxymethylated-30 kd GA733-2. Automated sequence analysis was performed on a model 470A gas phase microsequencer (Applied Biosystems) with on line PTH analysis using a Model 120A analyzer. Standard programs and reagents were used, except the reverse phase column for PTH amino acid analysis was a 5 um, 2.1×250 mm, LC-18-DB column (Supelco, Inc.).

Also, the latter part of the HPLC gradient was altered to separate PTH-trp from diphenylurea. Data was analyzed using a Nelson Analytical data acquisition system. The amino-terminal end of the 40 kd species was found to be blocked.

Amino acid analysis of the starting sample was used to estimate the amount of protein loaded on the sequencer utilizing PTC amino acid analysis after vapor phase hydrolysis (150° C., 1.0 hr, 6N HCl with 1% phenol, under argon and reduced pressure) essentially as described (Ebert, R. F. (1986) Anal. Biochem. 154, 431–435) except that a 3 um, 4.6×150 mm, LC-18-DB column (Supelco, Inc.) was used for the separation of PTC amino acid derivatives.

The amino acid sequence determined is shown in FIG. 3. Lower case letters indicate tentative determinations.

EXAMPLE 3

This example demonstrates the synthesis of an oligonucleotide probe for the GA733 gene family.

The amino-terminal 18 residues of the 30 kd form of GA733-2 were used for the design of a 54 base oligonucleotide probe, based on preferred codon usage in humans (Grantham, et al., (1981) Nucleic Acids Res. 9, r43-r74). The DNA probe had a 70% G+C content and included a 10 base palindromic structure. The oligomer 5' GTCGGGGTCGTACAGGCCGTCGTTGTTCT-GCAGGGCGCCCTCGGGCTTGGCCCT was synthesized by automated phosphoramidite chemistry on an Applied Biosystems model 380A DNA synthesizer. Full-length 54-mer was isolated by denaturing polyacrylamide gel electrophoresis and $C_{18}$ chromatography as described (Linnenbach, et al. (1986) Proc. Natl. Acad. Sci. USA 83, 2397–2401).

EXAMPLE 4

This example demonstrates the use of GA733 gene family probe for screening of a human genomic library.

A total human genomic library constructed by Lawn et al. (1978) Cell 15, 1157–1174 and obtained through the American Type Culture Collection (ATCC #37333) at the third amplification, was plated and plaques were transferred to nitrocellulose filters in duplicate. 0.5 ug of oligomer was 5'-phosphorylated in a 40 ul reaction mixture containing 0.05M Tris-Cl pH 7.6/0.01M MgCl/0.005M dithiothreitol/0.0001M spermidine/0.0001M EDTA/280 uCi of [gamma-$^{32}$P] ATP (5000 Ci/mMole; 1 Ci=3.7×10$^{10}$ becquerels), and T4 polynucleotide kinase at 37° C. for 45 min. The reaction mixture was adjusted to contain 0.02M EDTA/0.5% NaDodSO$_4$ the labeled oligomer was separated on a Sephadex G-25 column. Pre-hybridization and hybridization conditions for the use of the 54 base oligonucleotide were identical to those described previously for a 90 base probe (Linnenbach et al. supra).

Two different recombinants were identified using this probe, as determined by restriction enzyme analysis and by hybridization signal intensity. One of these recombinants was further analyzed. A restriction map for the 14.3 kbp genomic insert was based on analysis of partial digestion products of the Charon 4A recombinant. Aliquots of each partial digest were hybridized separately to $^{32}$P-end labeled oligonucleotides complementary to the phage left and right cohesive ends (Collaborative Research), and electrophoresed on a 0.4% agarose gel. The DNA fragments were transferred to a nitrocellulose filter and autoradiographed.

EXAMPLE 5

This example describes the method of sequencing and analyzing the gene for the GA733-1 antigen.

DNA sequencing was performed by the dideoxynucleotide method (Sanger et al., (1977) Proc. Natl. Acad. Sci. USA 74, 5463–5467) using T7 DNA polymerase (United States Biochemical Corporation). In order to resolve compressions, which were frequently observed in the coding region, templates were sequenced by the standard method in parallel with a method which substitutes dITP for dGTP.

The predicted amino acid sequence of the genomic isolate was evaluated for homology to known protein sequences using the program FASTP (Lipman et al., (1985) Science 227, 1435–1441) to search release 15.0 of the NBRF protein database. Sequences with the highest score were further evaluated with the program ALIGN, using the mutation data matrix (250 PAMs) (Dayhoff et al., (1983) in Methods in Enzymology, eds. Hirs, C. H. W. & Timasheff, N. (Academic Press, New York), 91, pp. 524–545). Unless otherwise indicated, the pairwise alignments were done using a gap penalty of 20. Alignment scores are expressed as standard deviation (s.d.) units above the mean score of 100 random runs. A score between 3-8 is indicative of a possible relationship; scores of below 8 are considered highly significant.

EXAMPLE 6

This example illustrates the isolation and characterization of the GA733-1 gene.

To target the initial DNA sequence characterization, genomic clone 05516 (FIG. 1A) was first subcloned into the Eco RI site of pBR322. The plasmid clone 05516-217 containing a 9.7 kbp Eco RI insert was shown by Southern blotting ((1978) J. Mol. Biol. 98, 50–517) to contain a 0.85 kbp Pst-1 restriction fragment which hybridized to the oligonucleotide probe (FIG. 1B). Initially, this Pst-1 fragment was sequenced to establish the identity of the 05516 clone. Analysis with the program BESTFIT (Devereux et al. (1984) Nucleic Acids Res., vol. 12, pp. 387–395) indicated that the oligomer hybridized with 05516 DNA at 35 (65%) of 54 positions, with a distribution of base pairing indicative of a related sequence (FIG. 2A).

An extended DNA sequence analysis of flanking restriction fragments (FIG. 1B) identified a GC-rich promoter region, including three GGGCGG hexanucleotides (FIG. 2A). In the context of a decanucleotide, one GC box is identical to that of the SV40 GC box IV, which has been characterized as a medium affinity site for the transcription factor Sp-1 (Kondonaga et al, (1986) Trends in Biochem. Sci. vol. 11, pp. 20-23), although direct experiments have not been carried out to determine if the GA733-1 promoter is in fact Sp-1 responsive. The promoter also has an atypical CAAT box (Efstratiadis et al., (1980) Cell, vol. 21, pp. 653–668), and a canonical TATA box.

A 323 amino acid protein is predicted with a molecular weight of 35,710 daltons, which is consistent with it being a member of a family of 40 kd glycoproteins.

A Kyte-Doolittle plot ((1982) J. Mol. Biol. vol. 157, pp. 105–132) of the predicted protein suggests the features of an integral membrane protein (FIG. 2B). A classic signal sequence (Perlman et al. (1983) J. Mol.

Biol. vol. 167, pp 391-409 and Watson, (1984) Nucleic Acids Res. vol. 12, pp. 5145-5159) is predicted with charged residues in the pre-core sequence, a 13 residue hydrophobic core sufficient to span a membrane, and a post-core region containing amino acids with small, uncharged side chains as candidate signal peptidase cleavage sites (FIG. 2A). Assuming that the signal peptidase recognition site is T-A-A, where cleavage would be located after the fourth amino acid following the core sequence, a 244 amino acid extracellular domain is predicted. A clustering of 12 cysteine residues, and four potential N-linked glycosylation sites are present in the extracellular domain. A single 23 residue transmembrane domain is followed by a 26 residue cytoplasmic domain, 9 of which are positively charged.

cDNA clones 1.8 kbp in length have been isolated; these clones are probably full-length, as their length correlated with the results of Northern blot experiments (see below). Based on restriction analysis (FIG. 1C) and preliminary DNA sequence, it has been determined that GA733-1 is an intronless gene. The 5' end residue of the full-length cDNA corresponds to a position in the gene sequence that is 53 bases from the TATA box (FIG. 2A), although the actual RNA start site has not been ascertained by a primer extension experiment. The 3' end of the cDNA is 13 residues after one of two possible polyadenylation signals.

Examination of the DNA sequence presented in FIG. 2A using the program REPEAT (Devereux, supra,) detected several eight base direct repeats. One in particular -TCCCAGAC- occurs directly before the probable RNA start site, and again in the 3' untranslated region before the poly(A) addition site. This suggests retrotransposition (Weiner, et al, (1986) Ann. Rev. Biochem, vol. 55, pp. 631-661) as a mechanism of gene duplication within this gene family.

EXAMPLE 7

This example demonstrates the expression of the GA733-1 antigen in gastrointestinal tumor cell lines.

Cytoplasmic poly(A)+ RNA was purified as described previously (Linnenbach et al., (1988) Proc. Natl. Acad. Sci. USA, vol. 85, pp 74-78) from human colorectal carcinoma cell lines SW948 and SW707; and from the pancreatic carcinoma cell lines BXPC-3 and Capan-2 (ATCC). mRNAs were denatured and electrophoresed by the method of Lehrach ((1977) Biochemistry, vol. 16, pp. 4743-4751), transferred to nitrocellulose filters and hybridized to a gel purified (Linnenbach (1986) supra,), nick translated, 0.85 kbp Pst-I genomic fragment derived from GA733-1.

Two pancreatic carcinoma cell lines were observed by Northern blot analysis to express larger amounts of a 1.8 kb mRNA species (FIG. 7, lanes 2 and 3), relative to the colorectal carcinoma cell line SW948 (FIG. 7, lane 1). When the Capan-2 pancreatic carcinoma mRNA was diluted 1:100 (lane 7), the hybridization signal was still more intense compared to that of SW948. This apparent difference in level of GA733-1 mRNA observed in these two cell types was normalized to enolase mRNA levels, which were observed to be constant in both cell types (FIG. 7, insert). Taking into account the relatedness of the GA733 genes, this experiment may not distinguish between transcription of GA733-2 mRNA and GA733-1 mRNA. In similarly controlled experiments, GA733-1 mRNA was detected in placenta but was not detected in the SW707 rectal carcinoma cell line, nor in the SK-mel-37 melanoma cell line.

I claim:

1. An isolated segment of DNA which codes for a protein having the amino acid sequence of the GA733-1 antigen.

2. The segment of DNA of claim 1 having the nucleic acid sequence shown in FIG. 2.

3. A cell line genetically engineered to replicate and express a DNA sequence which codes for a protein having the amino acid sequence of the GA733-1 antigen.

4. A method of producing a protein which has the amino acid sequence of the GA733-1 antigen comprising:

culturing cells in a culture medium, which cells have been genetically engineered to replicate and express a DNA sequence which codes for a protein which has the amino acid sequence of the GA733-1 antigen;

harvesting said protein from said cells or culture medium.

* * * * *

UNITED STATES PATENT AND TRADEMARK OFFICE
CERTIFICATE OF CORRECTION

PATENT NO. : 5,185,254
DATED : February 9, 1993
INVENTOR(S) : Alban Linnenbach

It is certified that error appears in the above-indentified patent and that said Letters Patent is hereby corrected as shown below:

TITLE PAGE, ITEM [56], REFERENCES CITED

After the heading PUBLICATIONS, please add the following references:

--Herlyn, et al., "Efficient Selection of Human Tumor Growth Inhibiting Monoclonal Antibodies, J. of Immun. Methods, 73:157-167 (1984)

DeFreitas, et al., "Human Antibody Induction to the Idiotypic and Anti-Idiotypic Determinants of a Monoclonal Antibody Against a Gastrointestinal Carcinoma Antigen", Current Topics in Microbiol. and Immunol., 119:75-89 (1985)

Herlyn, et al., "Specific Detection of Anti-Idiotypic Immune Responses in Cancer Patients Treated with Murine Monoclonal Antibody," J. of Immunol. Methods 85:27-38 (1985)

Canton, et al., "Comparative Sequence Analysis of CO17-1A Antigen-Specific Monoclonal Antibodies:, Hybridoma 5(1):S11-S16 (1986)

Herlyn, et al., "CO17-1A Antigen-Specific Monoclonal Antibodies: Their Production and Characterization", Hybridoma, 5(1):S3-S10 (1986)

Ross, et al., "Isolation and Characterization of a Carcinoma-Associated Antigen", Biochem. and Biophys. Research Comm., 135:297-303 (1986)

Herlyn, et al., "CO17-1A and Related Monoclonal Antibodies: Their Production and Characterization", Hybridoma, 5(1):S3-S10 (1986)

UNITED STATES PATENT AND TRADEMARK OFFICE
CERTIFICATE OF CORRECTION

PATENT NO. : 5,185,254
DATED : February 9, 1993
INVENTOR(S) : Alban Linnenbach

It is certified that error appears in the above-identified patent and that said Letters Patent is hereby corrected as shown below:

Linnenbach, et al., "Sequence Investigation of the Major Gastrointestinal Tumor-Associated Antigene Gene Family, GA733," Proc. Natl. Acad. Sci., USA 86:27-31 (1989)

Strand, "Molecular Cloning and Characterization of a Human Adenocarcinoma/ Epithelial Cell Surface Antigen Complementary DNA", Cancer Research 49:314-317 (1989)--

Signed and Sealed this

Fifteenth Day of February, 1994

Attest:

BRUCE LEHMAN

Attesting Officer  Commissioner of Patents and Trademarks